(12) United States Patent
Humayun

(10) Patent No.: US 8,177,777 B2
(45) Date of Patent: May 15, 2012

(54) SOFT TIP CANNULA AND METHODS FOR USE THEREOF

(75) Inventor: Mark S. Humayun, Timonium, MD (US)

(73) Assignee: Iridex Corporation, Mountian View, CA (US)

( * ) Notice: Subject to any disclaimer, the term of this patent is extended or adjusted under 35 U.S.C. 154(b) by 461 days.

(21) Appl. No.: 12/427,345

(22) Filed: Apr. 21, 2009

(65) Prior Publication Data

US 2010/0076271 A1    Mar. 25, 2010

Related U.S. Application Data

(63) Continuation of application No. 10/934,050, filed on Sep. 4, 2004, now Pat. No. 7,537,593, which is a continuation of application No. 09/982,549, filed on Oct. 18, 2001, now Pat. No. 6,800,076.

(60) Provisional application No. 60/241,496, filed on Oct. 18, 2000.

(51) Int. Cl.
A61F 9/007    (2006.01)

(52) U.S. Cl. ............................................. 606/4; 606/15
(58) Field of Classification Search .................. 606/4–6; 604/35, 264
See application file for complete search history.

(56) References Cited

U.S. PATENT DOCUMENTS

| | | | |
|---|---|---|---|
| 6,436,035 B1 * | 8/2002 | Toth et al. ..................... 600/249 |
| 6,491,670 B1 * | 12/2002 | Toth et al. ..................... 604/264 |

* cited by examiner

*Primary Examiner* — Roy Gibson
(74) *Attorney, Agent, or Firm* — Edwards Wildman Palmer LLP; Peter F. Corless; Lisa Swiszcz

(57) ABSTRACT

A surgical device having a body portion that is gripped by a user, the body portion having a distal end equipped with a soft tip and the proximal end optionally connected to an external vacuum or gas/air source. The surgical device is particularly suitable for use in ophthalmic surgical procedures to remove fluid from the eye or introduce gas/air into the eye. The soft tip is fabricated to protect the delicate tissues if the eye and is further modified so as to enhance a user's visibility of the device in the surgical field.

29 Claims, 7 Drawing Sheets

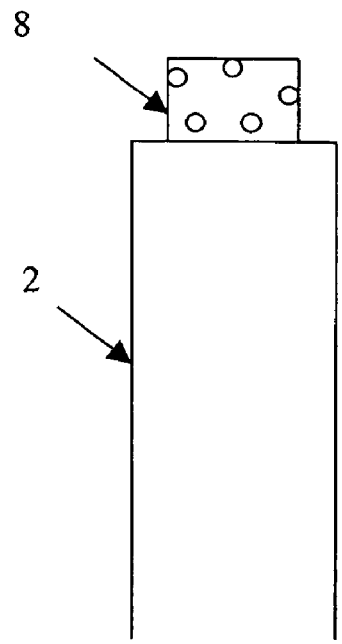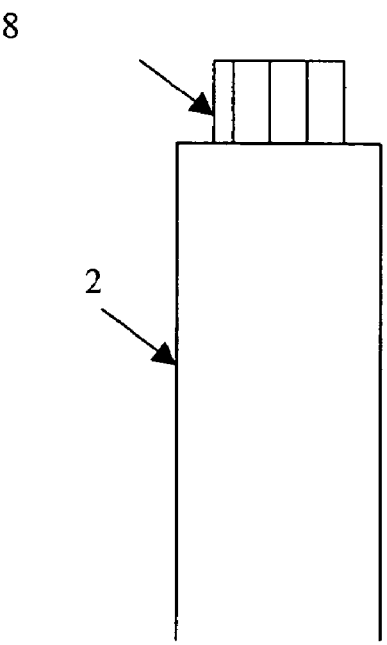
FIG. 5A  FIG. 5B
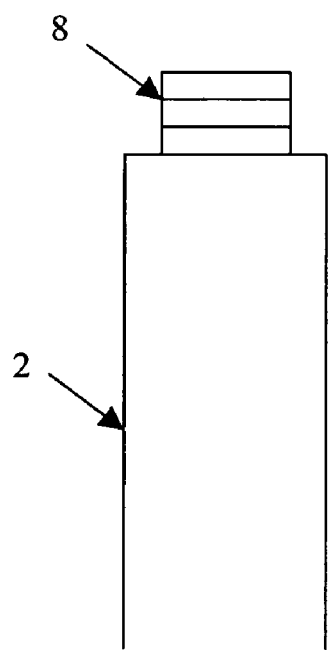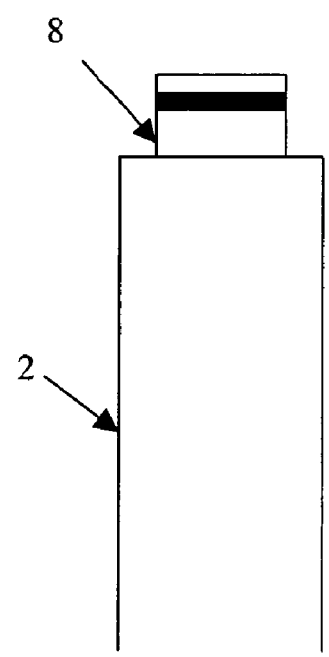
FIG. 5C  FIG. 5D

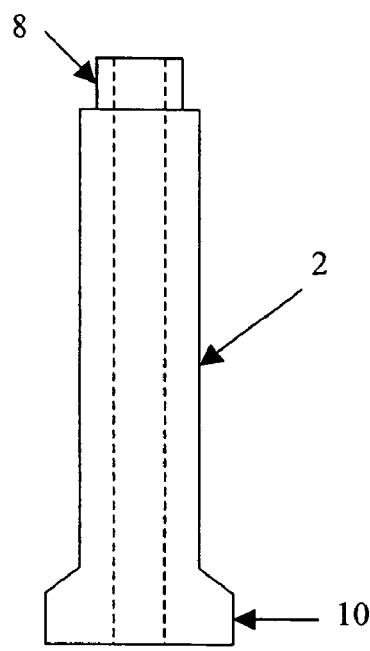
FIG. 6
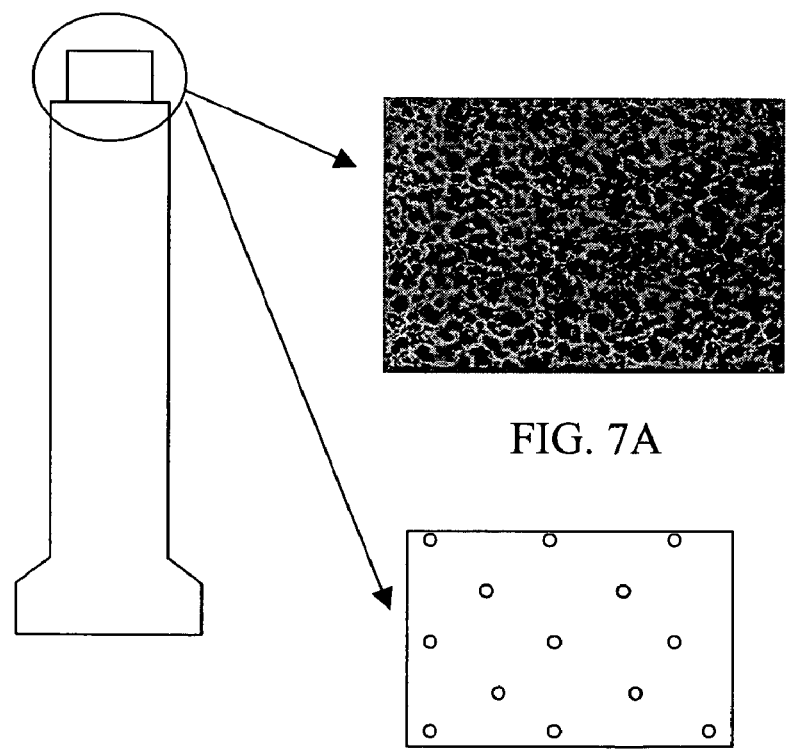
FIG. 7A
FIG. 7B

FIG. 8A
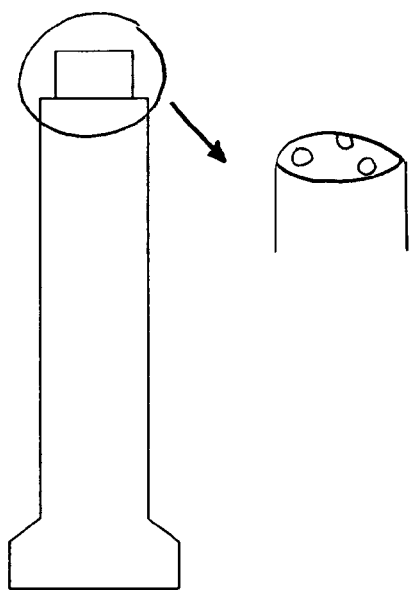
FIG. 8B
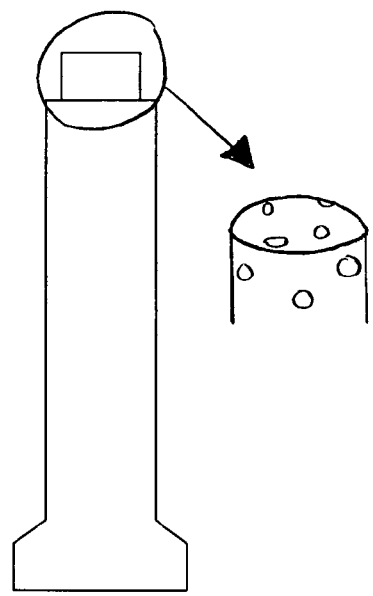
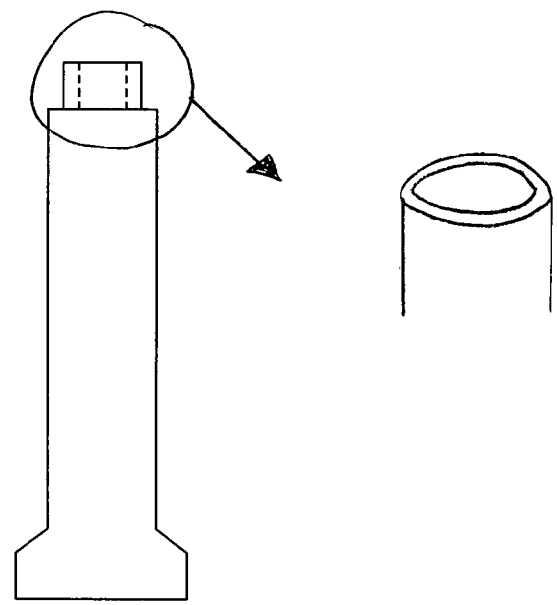
FIG. 8C

SOFT TIP CANNULA AND METHODS FOR USE THEREOF

This application claims the benefit of U.S. Provisional Application Ser. No. 60/241,496 filed Oct. 18, 2000, and is a continuation of and claims the benefit of and priority to U.S. patent application Ser. No. 09/982,549, filed on Oct. 18, 2001, now U.S. Pat. No. 6,800,076 which is a continuation of U.S. patent application Ser. No. 10/934,050, filed on Sep. 4, 2004, now U.S. Pat. No. 7,537,593, the entirety of which are incorporated herein by reference.

FIELD OF THE INVENTION

The present invention relates to a device used in connection with medical procedures, more particularly to cannulas used in ophthalmic procedures (e.g., retinal tear and retinal detachment surgery), as well as methods of use thereof.

BACKGROUND OF THE INVENTION

Cannulas are used in ophthalmic surgical procedures, such as retinal detachment surgery, to aspirate fluids such as blood, aqueous humor, and infused balanced saline solutions. The cannulas are typically connected by PVC tubing to a machine induced vacuum source and the fluids are collected in a disposable cassette in the machine. For ophthalmic surgical procedures, it is important that the cannula tip be specially designed for the delicate eye area. Thus, for example, such cannula tips are typically formed with rounded, smooth edges. Cannulas have also been made with a tip formed from a transparent soft material such as silicone. The soft silicone tip helps prevent damage to the delicate tissue of the eye in the event of physical contact with the eye.

Retinal detachment is a serious eye condition that, if not treated early, may lead to impairment or loss of vision. The condition typically affects older individuals, individuals with myopia (near-sightedness) and individuals with relatives having retinal detachment. In some instances, a hard, solid blow to the eye has lead to retinal detachment. Further, individuals who have undergone cataract surgery have, in some cases, subsequently developed retinal detachment.

The retina is a fine layer of nerve cells that covers the inside back portion of the eye (FIG. 2). If the retina thins, one or more small tears or holes in the retina may result (FIG. 3), leading to retinal detachment (FIG. 4). More often, retinal detachment is caused by shrinkage of the vitreous. The vitreous is a clear, gel-like substance that fills the inside of the eye and is firmly attached to the retina in several places. As the vitreous shrinks, as a result of age, inflammation, injury or near-sightedness, it often separates from the retina and, in some cases, it may pull a piece of the retina away with it, leaving a tear or hole in the retina. If the retina tears or breaks, watery fluid from the vitreous may pass through the hole and flow between the retina and the back wall of the eye producing "subretinal" fluid. Over time, the flow of the vitreous fluid between the retina and the back of the eye separates the retina from the back of the eye and causes it to detach (FIG. 4).

There are several procedures available to treat retinal detachment. The severity of the detachment or tear in the retina typically determines which of the procedures should be performed.

If the retina is torn but there is little or no retinal detachment, laser photocoagulation may be used to seal the retinal tears. During laser photocoagulation a laser is used seal the tear. Using the laser, small burns are placed around the edges of the tear. This produces scar tissue that seals the edges of the tear and prevents vitreous fluid from flowing through the tear.

Freezing or "cryopexy" is another procedure that is used to treat retinal tears. According to this procedure, the back wall of the eye behind the tear is frozen to produce scar tissue. As with laser photocoagulation, the scar tissue seals the edges of the tear and prevents vitreous fluid from flowing through the tear.

If the flow of the vitreous fluid between the retina and the back of the eye has caused the retina to detach, more complicated surgical procedures are required. In general, the detached portion of the retina is pressed against the back wall of the eye. Any subretinal fluid that is present must be drained from under the retina to allow the retina to settle back onto the back wall of the eye. The tears may then be sealed by use of, e.g., lasers, freezing, or an electrically heated needle which create scar tissue and seals the tear.

In severe cases, it is sometimes necessary to use a technique called vitrectomy. During this procedure, the vitreous body is cut away from the retina and removed from the eye. The vitreous cavity may then be filled with air or gas to push the retina back against the wall of the eye. In time, clear fluid from the blood seeps into and permanently fills the vitreous cavity.

During an ophthalmic procedure (e.g. retinal tear, retinal detachment, vitreoretinal procedure), the tip of a cannula is generally used to press a detached portion of the retina against the back wall of the eye, to fill the vitreous cavity with air or gas, and to remove the subretinal fluids from under the retina to allow the retina to return to its anatomically correct position.

A disadvantage of conventional cannulas is that the soft material of the cannula tip is transparent and, thus, difficult for the surgeon to discriminate during use, particularly during the fluid/air exchange when visibility is compromised by bubbles and a significant change in the refractive media from fluid to air.

There is a need for improved devices, systems and methods for use of these devices and systems during ophthalmic procedures. In particular, there is a need for improved devices, systems and methods for use during ophthalmic procedures wherein the device is easier for a user to detect and, thus, provides safe and easy manipulation around the particularly delicate eye area.

SUMMARY OF THE INVENTION

The present invention provides a novel surgical device and methods for use thereof.

More particularly, the present invention enables safe and easy manipulation of a surgical device during ophthalmic procedures (e.g., retinal tear and retinal detachment surgery), thereby minimizing the potential for damage to the delicate eye area.

In particular, the surgical device of the present invention is a soft tip cannula useful during ophthalmic surgery. The soft tip device may be an aspirating device or a non-aspirating device.

In a preferred embodiment, the surgical device is a soft tip cannula that assists in removing fluids during surgery. The soft tip cannula is particularly suitable for the removal of fluids from the posterior chamber of the eye during retinal detachment surgery.

In another embodiment, the surgical device is a non-aspirating soft tip device, such as a soft tip scraper cannula for assisting in the removal of membranes, such as the posterior hyaloid, internal limiting, and other membranes of the eye.

The soft tip device of the present invention provides enhanced visibility of the soft tip to the surgeon so that he/she may more easily manipulate the device safely and effectively.

According to one embodiment of the present invention, the properties of the typically transparent soft material comprising the soft tip portion of the device are modified in order to enhance visibility of the device to the surgeon.

In a preferred embodiment, the soft tip material is tinted, marked or stained to enhance visibility. The tinting, marking or stain is preferably of such a color that improves identification, visibility, position, and depth perception of the tip of the device. In one embodiment, the soft tip is stained with fluorescent material.

The entire soft tip may be tinted, marked or stained. Alternatively, the tip may be demarcated with an identifying mark, fiducial line, ring, characters, or stripe(s) to improve visibility/identification. One color or a combination of colors may be used as desired.

In preferred embodiments, the soft tip cannula is used with a fiber optic probe or similar illuminator by shining light from the fiber optic probe or similar illuminator onto the soft tip.

In another preferred embodiment, the soft tip cannula is connected to a fiber optic illuminator or a laser fiber and colored beams of light are transmitted by the soft tip to enhance visibility.

Other aspects and embodiments of the invention are discussed infra.

BRIEF DESCRIPTION OF THE DRAWINGS

FIGS. 5A-5D show various embodiments of a device in accordance with the present invention, wherein the soft tip is provided with one or more identifying marks (FIG. 5A), stripes (FIGS. 5A-C), and a fiducial ring (FIG. 5D).

FIG. 6 shows an embodiment of a device in accordance with the present invention, wherein the body portion is hollow.

FIGS. 7A-B show an embodiment of a device in accordance with the present invention, wherein the soft tip is formed of a porous material.

FIGS. 8A-B show embodiments of a device in accordance with the present invention, wherein the soft tip is provided with one or more apertures for passage of materials. FIG. 8C shows an embodiment of a device in accordance with the present invention, wherein the soft tip is hollow.

DETAILED DESCRIPTION OF THE INVENTION

Figure 1:
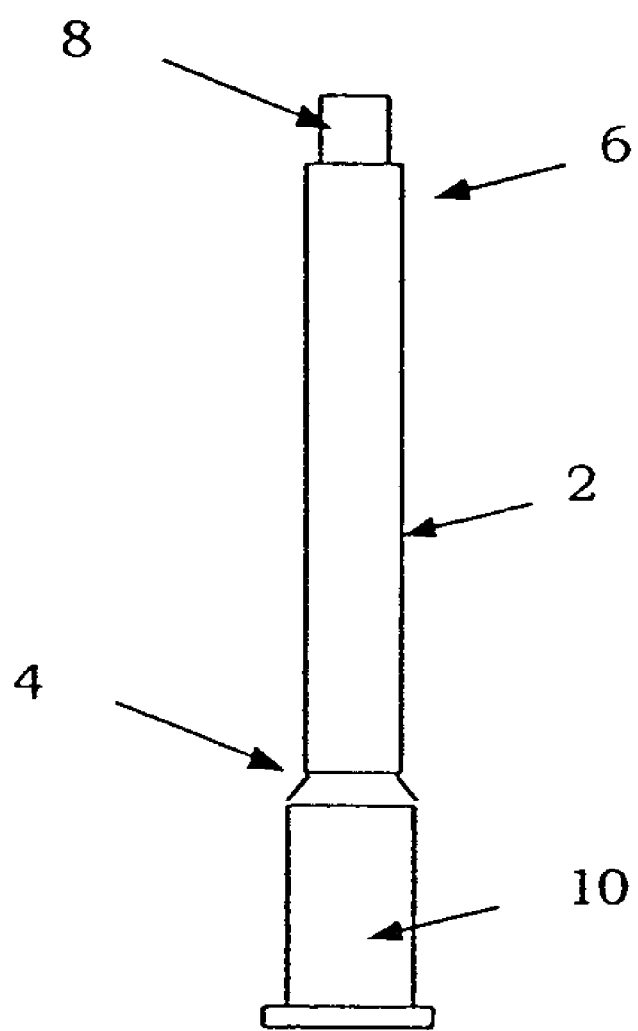
FIG. 1 is an isometric view of one embodiment of the soft tip surgical device of the present invention.
Figure 2:
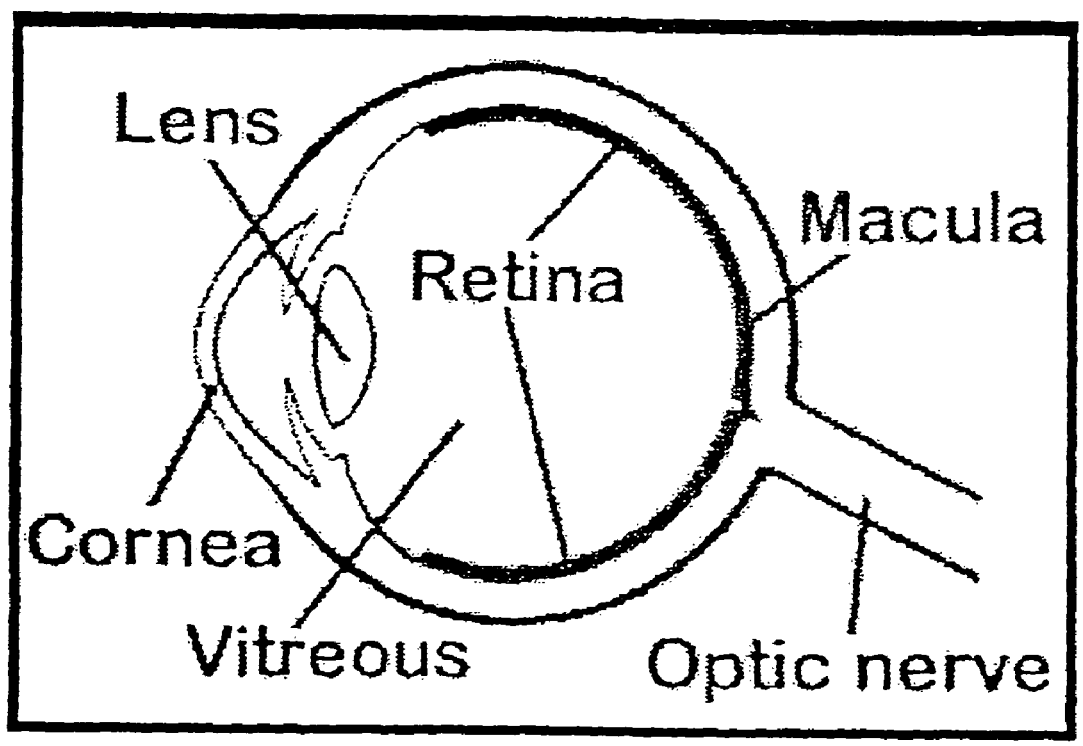
FIG. 2 shows a diagram of a normal, healthy eye.
Figure 3:
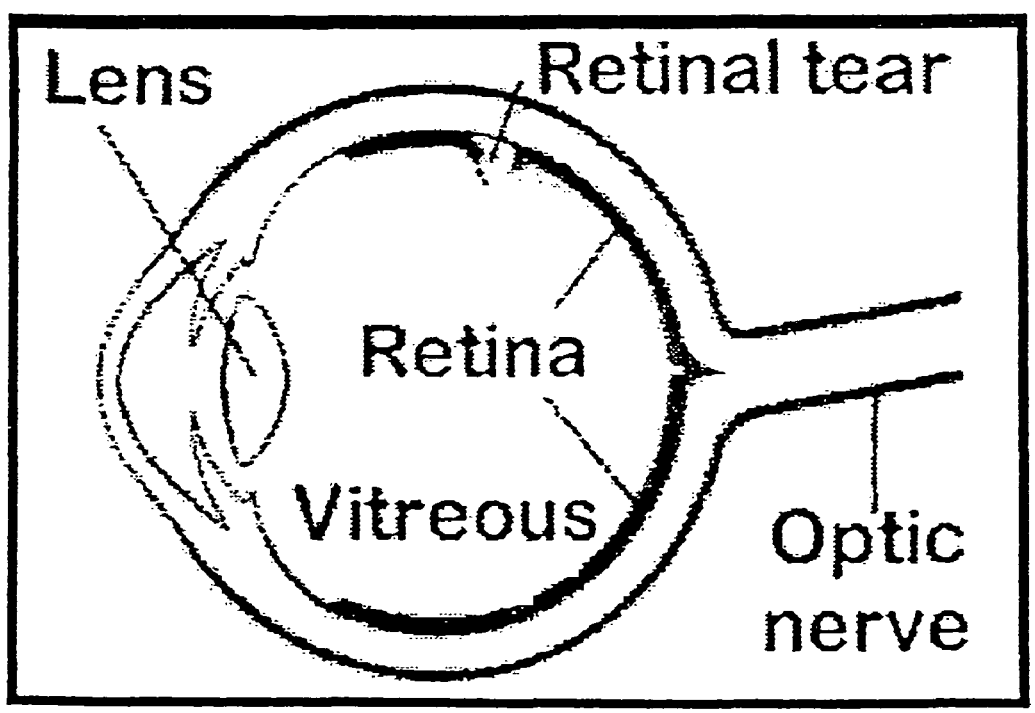
FIG. 3 shows diagram of an eye with a typical retinal tear.
Figure 4:
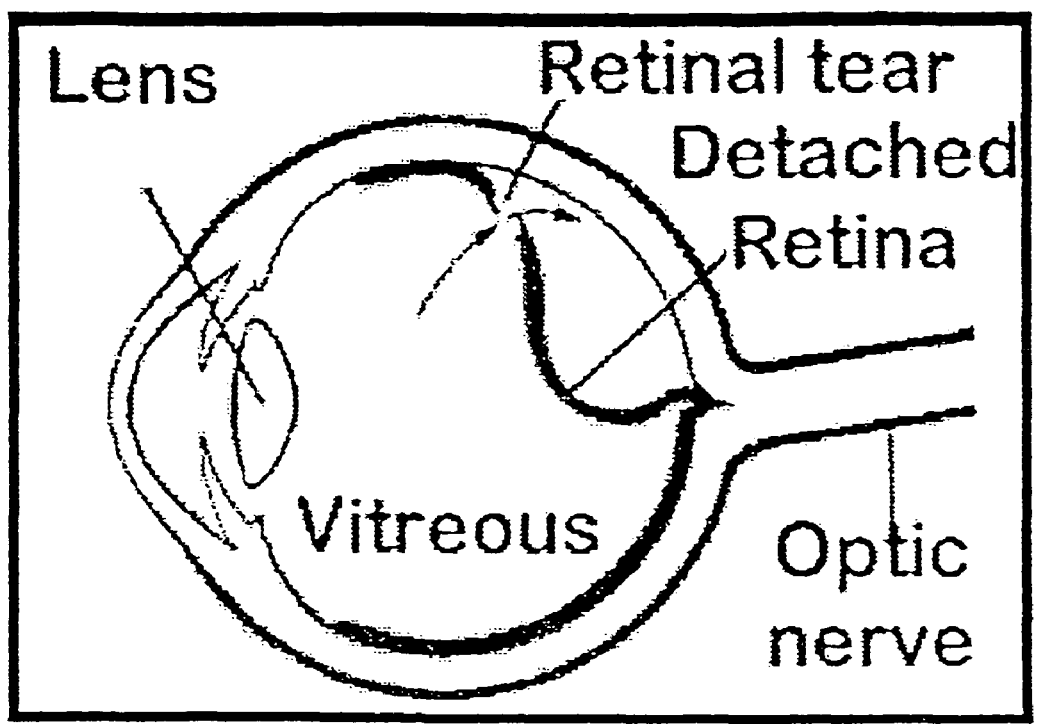
FIG. 4 shows diagram of an eye with a typical retinal detachment.

Referring now to the various figures of the drawing wherein like reference characters refer to like parts, there is shown in FIG. 1 various views of a soft tip surgical device 1 in accordance with the invention.

As shown, the soft tip surgical device 1 is in the form of a cannula, which may be aspirating or non-aspirating. Cannulas are well-known and, thus, although described below with reference to a preferred embodiment, the general features (e.g. size, shape, materials) of the soft tip surgical device 1 may be in accordance with conventional cannulas.

In a preferred embodiment, the soft tip surgical device 1 is designed for ophthalmic procedures. As such, the soft tip surgical device 1 comprises a body portion 2 having a proximal end 4, a distal end 6 and a soft tip 8 located on the distal end 6 of the body portion 2. A hub 10 may further be located on the proximal end 4 of the body portion 2.

In use, the soft tip surgical device 1 may be attached to a handle (not shown), which provides a user with further means for gripping the device 1. Such handles are known and are commonly referred to as extrusion handles. In the case of an aspirating device, the handle could be hollow so that fluid, gas and other material may flow through the handle. In the case of a non-aspirating device, the handle may be hollow or solid as desired. The handle may be attached to the soft tip surgical device 1 by a frictional fit and/or any conventional fastening means. The hub 10 portion may further be included and designed so as to assist in connecting the device 1 to the handle via a frictional fit and, if desired, any conventional fastening means may be used to assist the hub 10 in connecting the device 1 to the handle.

If desired, the handle may be omitted in an aspirating type device and, in such embodiments, the user may, for example, grip the device by the hub 10 and/or tubing connecting the device to a vacuum/aspiration source. In such an embodiment, the hub 10 portion may further be included and designed so as to assist in connecting the device 1 to the tubing via a frictional fit and, if desired, any conventional fastening means may be used to assist the hub 10 in connecting the device 1 to the tubing.

In use, the soft tip surgical device 1 is gripped by a handle, the tubing and/or hub 10 and the body portion 2 with the soft tip 8 is introduced into the surgical site. During an ophthalmic procedure, the soft tip 8 and body portion 2 enter the eye, for example, through an incision made in the eye to provide access to the retina at the back of the eye. Thus, the body portion 2 is preferably elongate in shape to provide easy access to the surgical site. Preferably, the body portion is designed so as to conform with the incision made in the eye (typically a 20 gauge incision) such that as the body portion 2 is inserted in the eye through the incision, the incision molds around the body portion and prevents leakage of materials into or out of the eye around the body portion 2. Further, the body portion 2 is preferably designed with a smooth surface so as to prevent further trauma to the eye as it is inserted through the incision. In one preferred embodiment, as shown in FIG. 1, the body portion 2 has an elongate cylindrical shape. The body portion 2 may have a substantially uniform cross sectional diameter or may taper. In one preferred embodiment, the body portion 2 tapers towards the distal end 6 to provide precision in placement of the soft tip 8. Although the body portion 2 is depicted as cylindrical in shape, other shapes may be used as desired. Additionally, the body portion 2 may include a bend (not shown) to provide easier access to areas that are difficult to reach.

The body portion 2 may be fabricated of any conventional materials used in forming similar surgical devices. Preferably, the material is lightweight and strong. Some conventional materials include plastics and stainless steel. Further, because the body portion 2 is inserted in the eye area in some applications, the materials used in forming the body portion 2 must be medically approved for such contact.

The soft tip surgical device 1 may be an aspirating device or a non-aspirating device. As a non-aspirating device, the body portion 2 may be hollow or solid.

As an aspirating device, the body portion 2 has a cavity through which fluids, gas and other materials may flow. The body portion further has a soft tip 8 at its distal end 6. Still further, tubing (e.g. PVC tubing) extending from the proximal end 4 of the body portion 2 (or hub 10 or handle, if included) connects the device to an external fluid or pressure source (e.g. Vitrectomy machine). The soft tip 8 is fabricated so as to maintain its shape and not collapse when the external fluid or pressure source is turned on. The soft tip 8 is further designed so as to allow the flow of fluid, gas and other materials through it. For example, the soft tip 8 may have one or more apertures, may be formed of a porous material or may be hollow.

In one embodiment, when used as an aspiration device, the soft tip 8 includes one or more slits or openings through which air, fluid and other materials may flow. The openings or slits may be of any geometric shape such as, for example, circular, oval or triangular. Preferably, the openings or slits are designed with rounded, smooth edges so as to not traumatize the delicate eye area in the event of contact with the eye. The number, size and placement of the openings or slits are not particularly limited, and may be in accordance with known aspirating cannulas for similar applications.

In another embodiment, the soft tip 8 is hollow and designed so that air, fluid and other materials may flow through the hollow soft tip 8 during use. As such, the hollow soft tip 8 may have any geometric shape and, for example, may be in the shape of a cylindrical hollow tube. During use, the soft tip surgical device 1 would be connected to an external fluid or pressure source, such as a vacuum/aspiration device. Materials from the eye would be aspirated through the open end of the hollow soft tip 8, through the hollow soft tip 8, through the cavity in the body portion 2 of the device, through the hub 10, through the handle, through the PVC tubing and, finally, the materials would reach a reservoir (e.g. a bag or chamber) at the vacuum/aspiration source.

To be used as an aspirating device 1, the proximal end 4 is designed so as to connect to an external fluid or pressure source. For example, the proximal end 4 may be designed for direct connection to tubing that connects the device 1 to an external fluid or pressure source. Thus, the proximal end 4 may be designed to have a frictional fit within or about the tubing. Conventional fastening means may also be used to secure the tubing to the proximal end 4. Alternatively, the proximal end 4 may be connected to the tubing via a conventional coupling device such as, for example hub 10. Further, if desired, the device 1 may be connected to a handle which, in turn, connects the device 1 to tubing.

The soft tip surgical device 1 is particularly suitable for use in ophthalmic surgical procedures. As such, the soft tip 8 may be formed of any material suitable for contact with the delicate eye area. Because the soft tip 8 is inserted into the eye area, the materials used in forming the soft tip 8 must be medically approved for such contact. Preferably, the soft tip 8 is formed of a soft, flexible and resilient material such as rubber or plastic. Silicone rubber and polyurethane are two examples of particularly suitable materials.

The soft tip 8 may be fixedly or removably connected to the body portion 2. Known means such as, for example, adhesives may be used to fixedly secure the soft tip to the body portion 2. The soft tip 8 may also be removably connected to the body portion by known means such as, for example, forming the soft tip 8 and the body portion 8 to have corresponding threaded portions that allows removable attachment of the soft tip 8 to the body portion 2. By providing a removable soft tip 8, the device may be reused by simply sterilizing the body portion 2 with ethelene oxide gas or similar means and replacing the soft tip 8 to maintain sterility and prevent cross-contamination between uses. More preferably, the entire device 1 is disposed of and replaced between uses to maintain sterility and prevent cross-contamination between uses.

According to the present invention, the soft tip 8 material is modified so as to enhance its visibility to a user while in the surgical field. In a preferred embodiment, the soft tip 8 material is colored, thereby improving identification, visibility, position and depth perception of the soft tip 8. Any colors may be used to optimize visibility of the soft tip 8 in the surgical field. Because the retina is generally orange-red in color, the soft tip 8 is preferably designed to provide maximum contrast on the orange-red background. Visualization and depth perception may be maximized by utilizing the science of optics and vision to select colors that will provide optimal contrast. Optimal contrast may be achieved by use of complimentary colors, as set out by Johannes Itten's color wheel developed in the 1930's. Thus, in a preferred embodiment wherein the soft tip 8 is utilized for retinal detachment surgery, the soft tip 8 would preferably be colored green-blue.

In one embodiment, the soft tip is coated or stained with a fluorescent material. Preferably, for use in retinal detachment surgical procedures, the soft tip 8 would have a green fluorescence. In another embodiment, the soft tip has an identifying mark, fiducial ring, character, stripes or other designs that improves visibility of the soft tip. These identifying marks, fiducial rings, characters, stripes or other designs are preferably selected so as to provide optimal contrast with relation to the background during use.

In another embodiment, the soft tip surgical device 1 is used together with a fiber optic probe or similar illumination mechanism, wherein the probe or illumination mechanism shines a light on the soft tip 8 to enhance its visibility in the surgical field.

In another embodiment, the soft material is connected to a light source, such as, for example, a fiber optic that illuminates the soft tip material so as to improve the visibility of the soft tip 8 while, at the same time, improving the visibility of the surgical field. For example, the light source may shine through the interior of the device and light up the soft tip 8 from within the soft tip 8.

In a preferred embodiment, an aspirating soft tip surgical device 1 has an overall length, from the soft tip 8 to the proximal end 4, ranging from about 28 to about 32 mm. More preferably, the soft tip surgical device 1 has a length ranging from about 29 mm to about 31 mm. The soft tip 8 portion of the device preferably has a length that ranges from about 2 mm to about 6 mm. More preferably, the length of the soft tip 8 portion of the device ranges from about 2 mm to about 3 mm. If included, the hub 10 preferably has a length ranging from about 10 mm to about 12 mm. In applications where the body portion 2 of the device is inserted into the eye through an incision, the diameter or thickness of the body portion 2 preferably conforms to the size of the incision so that the incision molds around the body portion 2 and prevents leakage of materials around the body portion 2. For example, in preferred embodiments, the diameter or thickness of the body portion 2 ranges from about 0.6 mm to about 1.2 mm. More preferably, the diameter or thickness of the body portion 2 ranges from about 0.8 to about 1.0 mm. However, it is to be understood that the diameter or thickness of the body portion 2 may vary depending on the particular procedure performed and the size of the incision made. In such applications where the body portion 2 is inserted into the eye through an incision, the length of the body portion 2 would be designed so that the soft tip 8 would reach the retina and back of the eye while allowing only the body portion 2, and not the hub 10, tubing or other apparatus connected to the proximal end 4 of the body portion 2, to enter the incision. If the device 1 is an aspirating device, the inner opening through which materials from the surgical site are suctioned preferably has a diameter ranging from about 0.2 mm to about 0.5 mm. More preferably the inner opening has a diameter ranging from about 0.25 mm to about 0.35 mm. Such dimensions are particularly suitable for optical procedures wherein the surgical area is delicate and can withstand limited suction and pressure. However, it is to be understood that various dimensions may be utilized depending on the desired suction and pressure limits for the particular application.

The soft tip surgical device 1 may be utilized during a retinal detachment surgical procedure as follows: an incision is made in the eye to provide access to the retina. The soft tip surgical device 1 in accordance with one embodiment is then inserted through the incision, with the soft tip 8 and the body portion 2 entering the incision. The device 1 could then be used to press the detached portion of the retina against the back wall of the eye. Additionally, the soft tip 8 may be embedded with abrasive materials to allow for scraping of scar tissue and eye tissues that are desirable to remove to increase visual acuity outcomes (e.g. ocular tissues: posterior hyaloid and internal limiting membrane "I.L.M.") As such, the device may be either a non-aspirating or aspirating device. If the device is non-aspirating, it is preferably removed and an aspirating soft tip surgical device 1 is then inserted into the eye. If the device is an aspirating soft tip surgical device 1, then the device remains in the eye.

During a vitreoretinal surgical procedure, after the vitreous body is cut away from the retina and removed from the eye, the aspirating soft tip surgical device 1 may be used to fill the vitreous cavity with air or gas to push the retina back against the wall of the eye. In such an application, the soft tip surgical device 1 would be connected to an air or gas source. The aspirating soft tip surgical device 1 can further be used to drain any subretinal fluid that is present between the retina and the back wall of the eye to allow the retina to settle back onto the back wall of the eye.

The present invention also includes kits that comprise one or more device of the invention, preferably packaged in sterile condition. Kits of the invention also may include, for example, one or more body portions 2, soft tips 8, etc. for use with the device, preferably packaged in sterile condition, and/or written instructions for use of the device and other components of the kit.

The following non-limiting example is illustrative of the invention.

EXAMPLE

Using the soft tip surgical device 1 and surgical technique of the present invention, three different surgeons performed vitreoretinal procedures. The surgeons evaluated the performance of the soft tip surgical device 1, the ability to visualize the distal soft tip 8 portion of the device during the fluid/air exchange portion of vitreoretinal procedures. During this procedure step visualization is difficult due to the mixture of air and fluid in the eye, which have different indexes of refraction.

The results were unanimous. All three surgeons evaluating the soft tip surgical device 1 indicated a dramatic difference in visualization of the soft tip 8 as compared to the traditional clear silicon soft tip cannulas. The surgeons indicated that the soft tip 8 appeared to be glowing or fluorescing when light from a fiber optic probe in their opposite hand was shone on the soft tip 8 and that the color provided significantly better contrast on the red-orange background of the retina. Insertion of a traditional clear tip cannula as a comparison did not result in good visualization.

The foregoing description of the invention is merely illustrative thereof, and it is understood that variations and modifications can be effected without departing from the scope or spirit of the invention as set forth in the following claims.

What is claimed is:

1. A surgical device particularly suitable for ophthalmic surgical procedures comprising:
   an elongate body portion;
   the elongate body portion having a proximal end and a distal end;
   a soft tip at the distal end of the body portion;
   the total length of the elongate body portion plus the soft tip being such that when the surgical device is inserted into the eye through any incision in the eye, the soft tip reaches the retina and back portions of the eye when only the soft tip and the elongate body portion enters the eye; and
   the soft tip having one or more markings to enhance a user's visibility of the soft tip in the surgical area.

2. The surgical device of claim 1, wherein the soft tip is formed of a soft material at least partially colored to enhance a user's visibility of the soft tip.

3. The surgical device of claim 2, wherein the soft tip material is at least partially colored with a fluorescent material.

4. The surgical device of claim 1, wherein the one or more markings is a fiducial ring.

5. The surgical device of claim 1, wherein the soft tip is connected to a light source that illuminates the soft tip.

6. The surgical device of claim 5, wherein the light source further illuminates the surgical site.

7. The surgical device of claim 5, wherein the light from the light source is transmitted by a fiber optic and illuminates the soft material.

8. The surgical device of claim 5, wherein the light source is a laser whose light is transmitted to the tip by a transmitting fiber.

9. The surgical device of claim 8, wherein the laser transmitting fiber transmits colored beams.

10. The surgical device of claim 1, wherein the body portion of the device is hollow and the device is an aspirating device.

11. The surgical device of claim 10, wherein the soft tip is formed of a porous material that allows material to be passed through.

12. The surgical device of claim 10, wherein the soft tip has one or more apertures through which material may pass.

13. The surgical device of claim 10, wherein the soft tip is hollow.

14. The surgical device of claim 1, wherein the device is a non-aspirating device for retinal manipulation or scraping of scar tissue or ocular tissues.

15. The surgical device of claim 1, further comprising a hub at the proximal end of the body portion.

16. The surgical device of claim 1, wherein the elongate body portion has a maximum diameter of about 1.2 mm.

17. The surgical device of claim 1, wherein the length of the elongate body portion is at least about 22 mm.

18. The surgical device of claim 1, further including one or more abrasive materials incorporated in the soft tip.

19. A medical device kit, comprising one or more of the surgical devices of claim 1.

20. The kit of claim 19, wherein the one or more delivery devices are packaged in sterile condition.

21. A method for performing an ophthalmic surgical procedure utilizing the device of claim 1 comprising:
   making an incision in the eye of a patient to access the treatment area;

inserting the device into the treatment area through the incision;

performing the ophthalmic surgical procedure; and removing the device from the treatment area, wherein the ability to visualize the soft tip during the ophthalmic surgical procedure is enhanced.

22. A surgical device particularly suitable for ophthalmic surgical procedures comprising:

an elongate body portion;

the elongate body portion having a proximal end and a distal end;

a soft tip at the distal end of the body portion; and the soft tip being modified so as to have one or more markings to enhance a user's visibility of the soft tip in the surgical area, the soft tip being connected to a light source that illuminates the soft tip.

23. A surgical device particularly suitable for ophthalmic surgical procedures comprising:

an elongate body portion having a proximal end and a distal end; and a soft tip at the distal end of the body portion;

the total length of the elongate body portion plus the soft top being such that when the surgical device is inserted into the eye through any incision in the eye, the soft tip reaches the retina and back portions of the eye when only the soft tip and the elongate body portion enters the eye;

the soft tip formed of a porous material that allows material to be passed through; and the soft tip being modified so as to enhance a user's visibility of the soft tip in the surgical area, wherein the elongate body portion is hollow and the device is an aspirating device.

24. The surgical device of claim 23, wherein the length of the elongate body portion is at least about 22 mm.

25. A surgical device particularly suitable for ophthalmic surgical procedures comprising:

an elongate body portion;

the elongate body portion having a proximal end and a distal end;

a soft tip at the distal end of the body portion;

the total length of the elongate body portion plus the soft top being such that when the surgical device is inserted into the eye through any incision in the eye, the soft tip reaches the retina and back portions of the eye when only the soft tip and the elongate body portion enters the eye; and the soft tip being modified so as to enhance a user's visibility of the soft tip in the surgical area, wherein the device is a non-aspirating device for retinal manipulation or scraping of scar tissue or ocular tissues.

26. The surgical device of claim 25, further including one or more abrasive materials incorporated in the soft tip.

27. A surgical device particularly suitable for ophthalmic surgical procedures comprising:

an elongate body portion;

the elongate body portion having a proximal end and a distal end;

a soft tip at the distal end of the body portion;

the total length of the elongate body portion plus the soft top being such that when the surgical device is inserted into the eye through any incision in the eye, the soft tip reaches the retina and back portions of the eye when only the soft tip and the elongate body portion enters the eye; and the soft tip being modified so as to enhance a user's visibility of the soft tip in the surgical area, wherein the device is an aspirating device for retinal manipulation or scraping of scar tissue or ocular tissues.

28. The surgical device of claim 27, further including one or more abrasive materials incorporated in the soft tip.

29. The surgical device of claim 27, wherein the length of the elongate body portion is at least about 22 mm.

* * * * *